United States Patent [19]

Linn

[11] Patent Number: 4,492,572
[45] Date of Patent: Jan. 8, 1985

[54] MELTING CRUCIBLE

[75] Inventor: Horst Linn, Hirschbach, Fed. Rep. of Germany

[73] Assignee: Linn Elektronik GmbH, Hirschbach, Fed. Rep. of Germany

[21] Appl. No.: 366,987

[22] Filed: Apr. 9, 1982

[30] Foreign Application Priority Data

May 12, 1981 [DE] Fed. Rep. of Germany ....... 3118750

[51] Int. Cl.³ .......................... F27B 14/00; B65D 5/72; C21B 3/00
[52] U.S. Cl. .................................... 432/263; 222/572; 266/275; 432/156
[58] Field of Search ............... 432/263, 156, 157, 262; 222/572; 266/275

[56] References Cited

U.S. PATENT DOCUMENTS 1,347,984 7/1920 Astrom ................................ 222/572
3,705,712 12/1972 Yerouchalmi ...................... 222/572

FOREIGN PATENT DOCUMENTS 463041 4/1951 Italy ................................... 432/262

Primary Examiner—John J. Camby
Attorney, Agent, or Firm—Louis E. Marn

[57] ABSTRACT

A melting crucible for small amounts of material has a plurality of pouring openings for the discharge of material selectively from the crucible, or comprises a ring member which is connected to a lower crucible portion containing the material, and which has at least one pouring opening for selective discharge of material from the crucible portion.

12 Claims, 8 Drawing Figures

MELTING CRUCIBLE

BACKGROUND OF THE INVENTION

This invention relates to melting crucibles or pots, more particularly for use in processing small amounts of material, such as for dental technology and analytical purposes and for preparing samples for metallurgical purposes. In this specification, reference to small amounts of material to be processed in such a crucible means the amounts which are usually employed for example in analytical operations and in dental technology, and generally in laboratory operation, for example amounts of not more than 2 kg.

Melting crucibles or pots for such purposes may have only a single pouring or discharge opening, for example in the region of the upper edge of the crucible, or no pouring opening at all. In either situation, it has been found that the service life of such a crucible is frequently relatively short, for the reason that the wall of the crucible is eroded to an excessive degree and at an excessive speed, during pouring operations, in the region of the pouring opening, so that the wall of the crucible may be totally destroyed in the region of the pouring opening or spout.

SUMMARY OF THE INVENTION

An object of the present invention is to provide a melting crucible or pot, which does not suffer from the above-indicated disadvantage.

A further object of the invention is to provide a melting crucible which has an enhanced service life in comparison with previously known melting crucibles or pots.

Yet another object of the invention is to provide a melting crucible which is particularly appropriate for analytical and dental operations and for sample preparation for metallurgical purposes.

A still further object of the invention is to provide a melting crucible which is resistant to erosion phenomena.

Yet another object of the present invention is to provide a melting crucible which permits the wear of the crucible caused in use thereof by the material being processed therein to be reduced by being spread over a larger area of the crucible itself.

Still another object of the present invention is to provide a melting crucible or pot for processing small amounts of material, which comprises a number of interconnected members or portions, thereby facilitating manufacture of the crucible and enhancing the possible range of materials from which the respective portions or members may be manufactured, in order better to adapt them to their respective functions.

These and other objects are achieved by means of a crucible for small amounts of material, which has at least two pouring openings in the region of the upper edge of the crucible. The provision of a plurality of pouring openings means that the service life of the crucible can be many times longer than the service life of previous crucibles which have only one pouring opening. This means that either the amount of material consumed in making the crucibles, more particularly in regard to crucibles which are not reconditioned after a period of use, is reduced, or reconditioning costs can be correspondingly reduced as the need for reconditioning the crucible will occur only after a substantially longer service life. It will be appreciated that the importance of a long service life before disposing of the crucible or before reconditioning thereof is of very great significance more particularly in regard to crucibles for analytical and dental purposes and for preparing samples for metallurgical operations, as such crucibles are frequently made from extremely high-cost material, for example noble metal. When a crucible is made from a noble metal, for example a platinum-gold alloy, as may be used in analysis processes, the reconditioning costs alone for example may be extremely high, in relation to the capacity of the crucible which may be only for example about 10 cubic centimeters.

In an alternative form of the crucible, the crucible may be of such a construction as to comprise a lower portion or container portion, for containing the material to be processed, and a pouring ring member which has at least one pouring opening and possibly a plurality thereof. The ring member engages around the container portion of the crucible, around the upper edge at the mouth opening thereof, thereby to support the container portion.

With a crucible of this kind therefore, the crucible is divided into two members or portions, more particularly the bottom portion which forms the actual crucible container portion itself, and the pouring or discharge ring on which the container portion is mounted and which is movable relative to the container portion. With this construction, the pouring ring and the container portion may be rotated relative to each other, whereby the pouring opening of the pouring ring may be moved to a position at which the container portion of the crucible is still of sufficient wall thickness. This therefore spreads the load produced by pouring material from the container portion, over the entire periphery of the wall of the container portion. It will also be appreciated that such a construction could be applied to known crucibles which are of a generally egg-cup shape and which do not have an actual pouring opening, in order thereby to provide such a crucible with a pouring opening. This is advantageous with regard to certain areas of use, as in that case the molten material issues from the crucible at an accurately defined position, by virtue of passing through the pouring opening instead of merely spilling over the edge of the mouth opening of the crucible. It will also be appreciated that either the pouring ring member or the container portion may be renewed separately from the other of those two components, according to circumstances such as the respective rate of wear, while the pouring ring and the container portion may be made of a material which is best adapted to the particular function to be performed by each of those two components, instead of the compromise material which may have to be used to make a one-piece crucible.

When the crucible comprises a separate pouring ring, in principle it would be sufficient to provide just one pouring opening, since the position of discharge of the material from the crucible can be altered by rotating the ring member relative to the container portion of the crucible. However, it may be advantageous for the pouring ring to have a plurality of pouring openings, as that will contribute to enhancing the service life of the pouring ring. Another advantage of the two-part construction of this crucible is that manufacture is also simplified, as it is easier to produce a bottom or container portion which is of comparatively simple configuration, and, separately therefrom, the pouring ring providing the pouring opening or openings. As mentioned above, it is also possible to produce the container portion and the pouring ring from different materials, because of the different loadings applied to the container portion and the pouring ring in operation thereof, more particularly since the molten material comes into contact with the pouring ring only for a relatively short period of time, while the material is being poured out.

It should also be observed at this point that the service life of a two-part crucible is probably going to be longer than the service life on the one-piece crucible having a plurality of pouring openings, as in practice the number of pouring openings which can be provided in the one-piece crucible is subjected to certain limits, for example for reasons of space as well as for reasons of stability and strength of the crucible, and manufacturing costs. In practice, it appears to be unlikely that more than eight pouring openings would be provided in the one-piece construction. On the other hand, when the crucible has a separate pouring ring, as referred to above, it would be possible to use any number of rings with one and the same container portion, or possibly vice-versa.

In an embodiment of the invention, the bottom or container portion and the pouring ring member can be readily interconnected to form the crucible assembly by the container portion having an outwardly projecting flange portion which extends at least part of the way around the edge of the mouth opening of the container portion and which may extend entirely therearound. The pouring ring member may then have suitable means for co-operating with the flange portion, for example one or more recesses in the appropriate part of the pouring ring to receive the flange portion, or an inwardly extending flange portion co-operable with the flange portion on the container.

It is also desirable for the container portion and the pouring ring member of the two-part construction to be adapted to each other such that the cross-section of said at least one pouring opening in the pouring ring member is arranged entirely above the upper edge of the mouth opening of the container portion; in other words, the cross-section of the pouring opening or openings is not restricted or reduced by the container portion partially masking the opening or openings.

It may be desirable for the crucible to be of a rotataionally symmetrical configuration, whether of the one-piece or two-piece construction, and in that case it is also advantageous for the crucible to have at least four pouring openings which are distributed over the periphery of the crucible or the periphery of the pouring ring. As mentioned above, under practical circumstances it is unlikely that the number of pouring openings provided in the crucible, which is of comparatively small size, will be more than eight.

In order to ensure that the thermal loading on the crucible is rendered as uniform as possible, in order thereby to reduce the possible detrimental effect of such a loading on the crucible, and also to minimise the problems which might be encountered in manufacture of the crucible, it is desirable for the pouring openings to be arranged at substantially equal spacings from each other.

In accordance with another feature of the invention, use of the crucible according to the invention will be facilitated if all the pouring openings of the crucible of the pouring ring member, in the case of the two-part construction, are of substantially identical configuration so that any pouring opening can be used in a pouring operation, without otherwise affecting operation of the installation.

In accordance with yet another feature of the invention, the pouring opening or openings may be of a spout-like or nozzle-like configuration, in the form for example of a tubular extension portion extending from the crucible or the pouring ring member, thereby to facilitate the discharge flow of material, especially in certain situations of use.

It will be appreciated that a crucible constructed in accordance with the principles of this invention can be used virtually for all areas of use. The crucible can be in virtually any small-scale casting installations, irrespective of the particular nature of the casting operation and the particular nature of the casting to be produced, for example whether the casting to be produced is a centrifugal or spun casting, a pressure casting, a vacuum casting, a vacuum-pressure casting or a casting produced by tipping, as in an open mould. The material to be processed in the crucible may also be heated in any manner, so that the conventional heating means using a flame, induction currents, an electric arc (plasma), an electron beam, a laser beam, or direct or indirect electrical resistance heating can be employed. The crucible in accordance with the invention may also be manufactured from any usual material or materials. Thus, the crucible can be manufactured from ceramic material (with or without fibre additive), glass ceramic, metal ceramic, quartz, graphite, carbon, glass graphite as well as metal and noble metal alloys, for example platinum, possibly alloyed with Rh, Zr or Au and zirconium and alloys, titanium, tungsten, copper and copper alloys. The crucible in accordance with the principle of the invention may also be produced in widely varying forms, for example in the form of a trough-like or cradle-like crucible, an upright crucible, a shuttle-like crucible, a divisible crucible, a crucible for the operation referred to as skull melting, crucibles with flat, spherical or elliptical bottoms and crucibles with a wide range of angles of wall inclination or curved wall shape.

DESCRIPTION OF THE PREFERRED EMBODIMENTS

Figure 2:
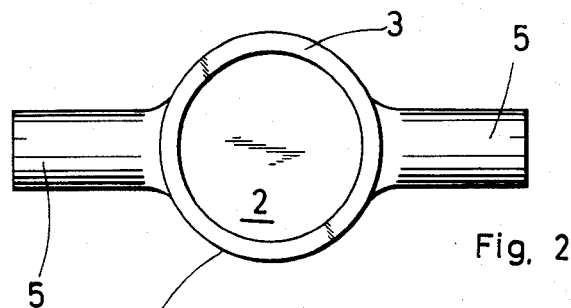
FIG. 2 shows a plan view of the FIG. 1 crucible.
Figure 1:
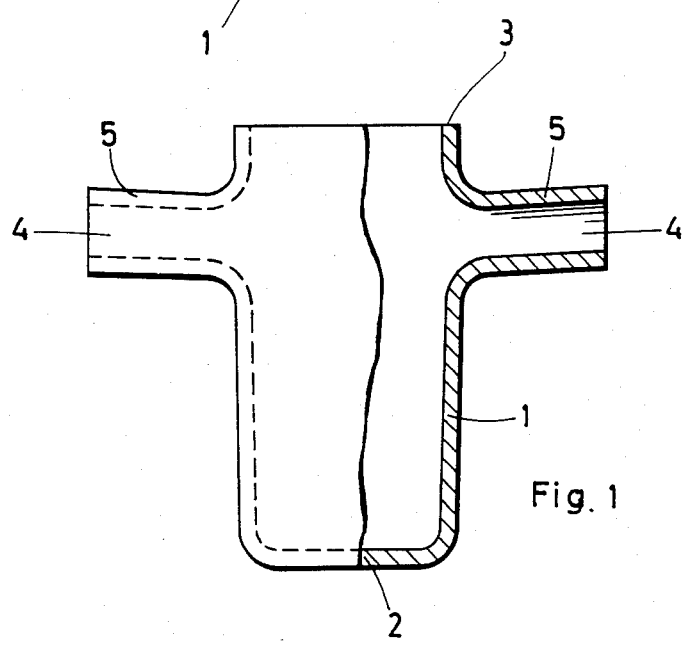
FIG. 1 shows a side view in partial section of a first embodiment of a melting crucible or pot having two oppositely disposed discharge or pouring openings of a spout-like configuration.

Referring firstly to FIGS. 1 and 2, a melting crucible or pot comprises a container portion having a substantially cylindrical wall portion or casing 1 and a substantially flat bottom 2. Formed on the container portion 1, 2 is an upper portion defining a mouth opening having an edge as indicated at 3. Provided in the upper portion of the crucible, adjacent the mouth opening edge 3, are two pouring or discharge openings 4 which, as illustrated, are disposed substantially diametrically opposite to each other and which are formed by respective nozzle-like or spout-like extension tube portions 5. As can be seen from the drawing, the portions 5 are comparatively long which permits the crucible shown in FIGS. 1 and 2 to be fitted for example into a heat-insulating jacket or into the coil of an induction heating means, or which permits the metal to be conducted over greater distances in being discharged from the crucible, which may be necessary under certain circumstances such as the configuration of the installation in which the crucible is to be used.

Figure 4:
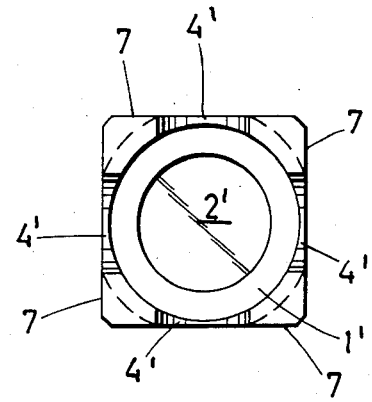
FIG. 4 shows a plan view of the FIG. 3 construction.
Figure 3:
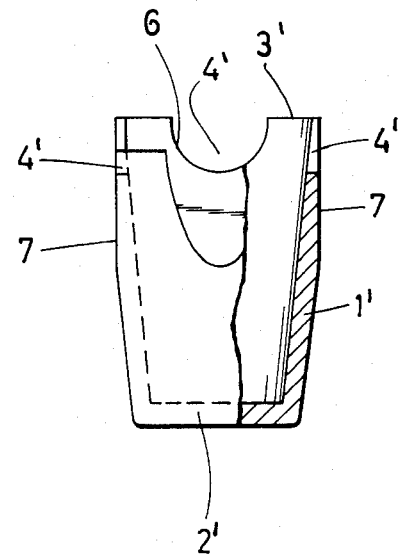
FIG. 3 shows a side view in partial section of a second embodiment of a crucible or pot, comprising pouring openings formed by recesses or notches.

Reference will now be made to FIGS. 3 and 4 showing a comparatively simpler embodiment of the crucible. As can be seen most clearly from FIG. 3, the casing portion or container portion 1' tapers inwardly in a downward direction. The pouring openings 4' are formed by part-circular recesses 6 formed in the upper edge 3 of the crucible, around the mouth opening thereof.

It will also be seen from FIGS. 3 and 4, that, while the casing portion 1' is of a downwardly tapering configuration, it is flattened in its upper region as indicated at 7, in such a way as to form four lateral contact or support surfaces which are disposed at an angle of 90° relative to each other, the angular arrangement of the surfaces at 7 being most clearly visible from FIG. 4. The surfaces 7 can be used for example to grip the crucible in a casting installation.

Figure 6:
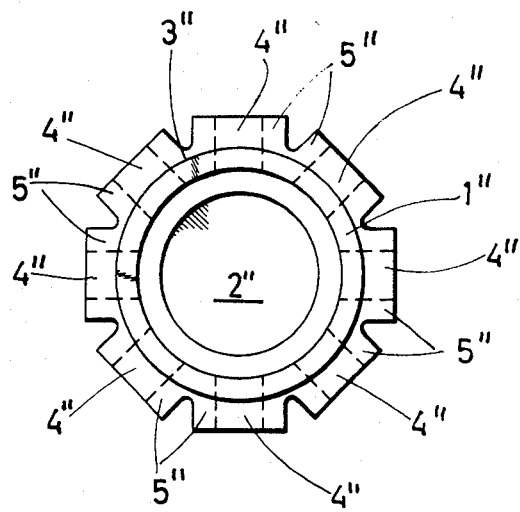
FIG. 6 shows a plan view of the FIG. 5 construction.
Figure 5:
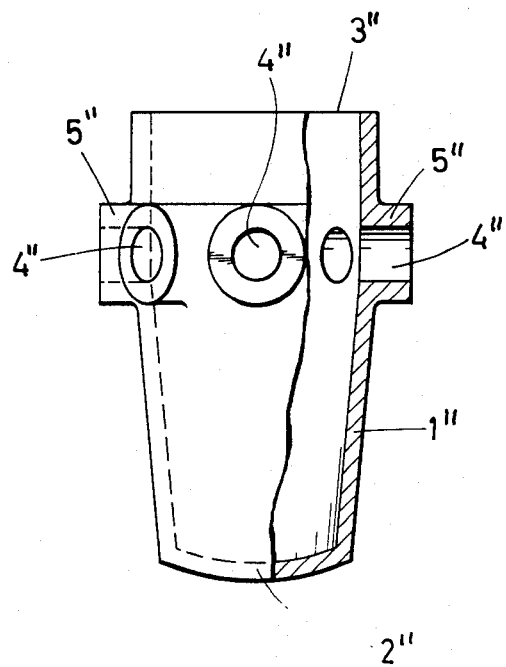
FIG. 5 shows a side view in partial section of a further embodiment of a crucible or pot having eight pouring openings.

Referring now to FIGS. 5 and 6, this embodiment of the crucible is generally similar to that shown in FIGS. 1 and 2, but comprises eight pouring or discharge openings 4" which are also formed by spout-like or nozzle-like tube portions 5", as shown in FIGS. 1 and 2. The openings 4" are disposed in the upper third of the crucible, adjacent the edge 3" of the mouth opening of the upper portion of the crucible, and are distributed over the periphery of the crucible in a uniform arrangement, that is to say, with at least substantially equal angular spacings between each two adjacent openings.

The casing or container portion 1" of the crucible shown in FIGS. 5 and 6 is of a slightly tapered configuration in a downward direction, similar to the crucible shown in FIGS. 3 and 4. The bottom 2" of the container portion of the crucible is of an outwardly, that is to say, downwardly, curved configuration, as shown most clearly in FIG. 5.

Figure 8:
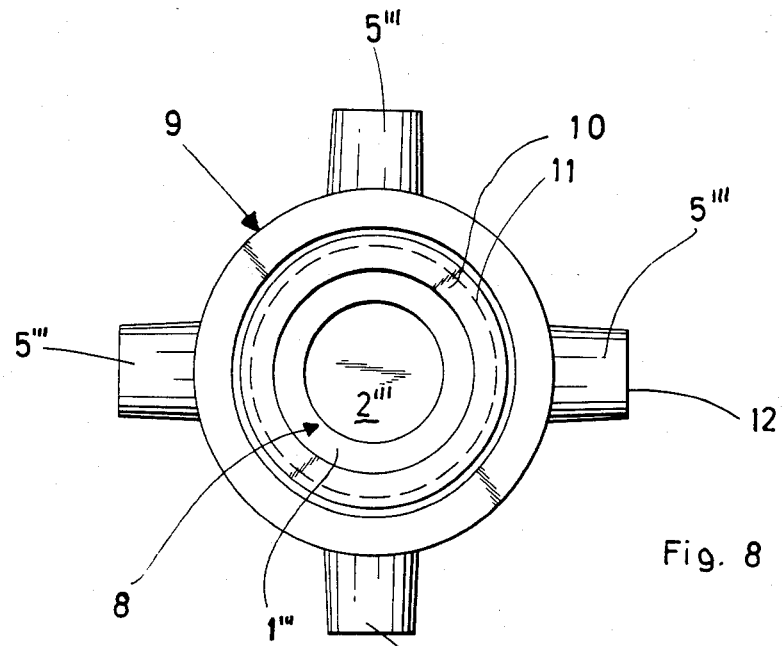
FIG. 8 shows a plan view of the FIG. 7 construction.
Figure 7:
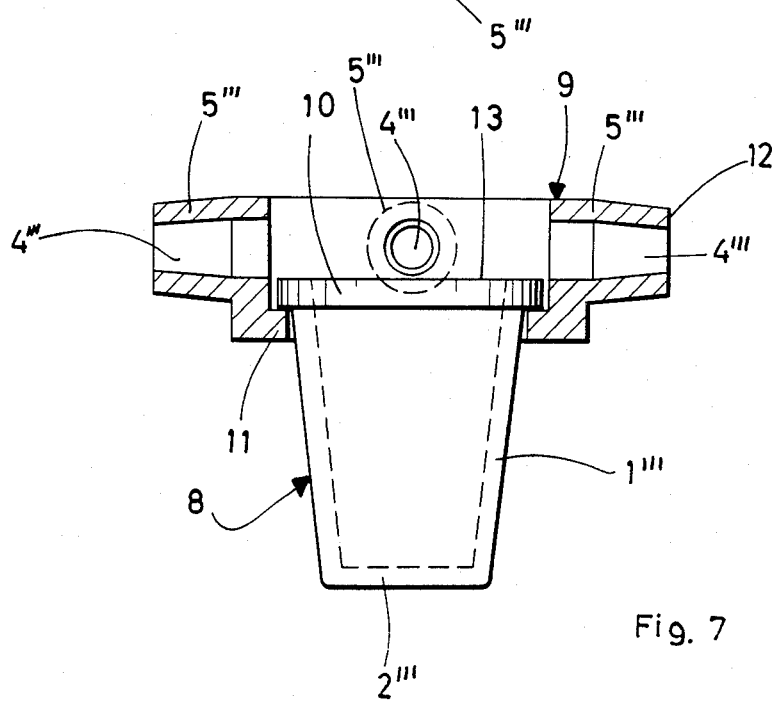
FIG. 7 shows a partly sectional view of a two-part crucible or pot having four pouring openings.

While the crucibles shown in FIGS. 1 through 6 are all of a one-piece or integral construction, with a plurality of pouring openings to provide the possibility of selectively pouring the material from the container portion at a number of locations, thereby to avoid overloading and thus eroding the material of the crucible, FIGS. 7 and 8 show a crucible or pot which comprises an assembly of two components, namely a bottom or container portion 8 and a pouring ring member 9. The container portion 8 is of a similar configuration to the crucible shown in FIGS. 3 and 4, that is to say, the casing portion 1''' thereof is of a downwardly tapering configuration. The bottom 2''' of the crucible is flat, as can be seen from FIG. 7. The container portion 8 does not have any pouring opening in the side thereof, but only the mouth opening at the upper end thereof.

Around the edge of the mouth opening at the upper end of the container portion 8 is a flange portion 10 which extends generally radially outwardly from the container portion 8. The flange portion 10 may extend entirely around the edge of the mouth opening of the container portion 8, or may be formed by a number of flange sections, so that the flange portion 10 thus extends around part of the periphery of the container portion 8.

The pouring ring member 9 has a flange portion 11 which extends inwardly of the aperture formed by the ring member 9 and which extends around the periphery of that aperture, although the flange portion 11 could be formed by a number of flange sections, instead of a peripheral flange portion, in a similar manner to the flange portion 10 on the container portion 8. It will be noted from FIG. 7 that the flange portion 11 is disposed in the bottom part of the ring member 9 as illustrated in the drawing. The flange portion 10 is supported on the flange portion 11, whereby the members 8 and 9 are interconnected, at least in such a way that the container portion 8 can be lifted by raising the ring member 9.

It will be appreciated that it would be readily possible to provide another way of connecting together the container portion 8 and the pouring ring 9, for example by projections on the container portion 8, which engage into suitable recesses in the pouring ring member 9.

In the embodiment illustrated in FIG. 7, the pouring ring member 9 has four discharge or pouring openings 4'''' which, similarly to the embodiments shown in FIGS. 1, 2 and FIGS. 5, 6, are each formed by a spout-like extension tube portion 5''''. As can be clearly seen from FIG. 7, the tube portions 5'''' taper slightly in extending outwardly from the centre of the pouring ring member 9, that is to say, the transverse dimension of the opening formed by each tube portion 5'''' decreases in a direction towards the free outside end thereof, as indicated at 12. It will be appreciated that such a tapered configuration is not a necessary feature, and that the opening in the tube portion 5'''' could be of a uniform dimension throughout. It will also be appreciated that various other forms and configurations of the pouring opening or openings in the pouring ring member 9 could also be employed. For example, instead of the spout-like tube portions 5'''' illustrated for example in FIG. 7, it would be possible simply to provide channel means or just notches or recesses.

FIG. 7 shows that the dimensions of the container portion 8 and the pouring ring 9 are such that the cross-section and thus the discharge flow area of each of the openings 4'''' is disposed completely above the upwardly facing surface of the upper edge 13 around the mouth opening of the container portion 8. This is achieved by suitable selection in respect to the height of the flange portion 10 and suitable positioning of the flange portion 11 at the underside of the pouring ring member 9.

Still with reference to FIGS. 7 and 8, the nature and configuration of the container portion 8 and the pouring ring member 9 may be varied to adapt them to the respective requirements to be imposed thereon. For example, the container portion 8 and the pouring ring member 9 may possibly be produced from different materials, so as to adapt each of those two components to the different loadings and requirements to which they are subjected, both in manufacture and in operation of the crucible, whereby the service life and also the areas of use of the crucible may be substantially enhanced and enlarged. The arrangement and the number of pouring openings 4'''' in the ring member 9 and also the configuration thereof may also be varied from those illustrated.

It will be understood that the above-described embodiments of the crucible according to the invention, and modifications therein, are described solely by way of non-limiting example and that further and different alterations and modifications may be made therein without thereby departing from the scope and spirit of the present invention.

What is claimed is:

1. A melting crucible assembly for accommodating small amounts of material particularly for dental, analytical and metallurgical purposes, which comprises:
    a container portion having a mouth opening and an upper edge portion for accommodating said material; and
    a pouring ring having at least one pouring opening, said pouring ring engaging said container portion about said upper edge portion thereof.

2. The crucible assembly as set forth in claim 1 wherein said container portion has, at the edge of the mouth opening thereof, an outwardly projecting flange portion which extends at least partly around said mouth opening, and wherein said pouring ring cooperates with said flange portion for suspending said container portion from said pouring ring.

3. The crucible assembly as set forth in claim 2 wherein said pouring ring is provided with an inwardly projecting flange portion.

4. The crucible assembly as set forth in claim 2 wherein said pouring ring includes at least one recess for receiving said flange portion of said container portion.

5. The crucible assembly as set forth in claim 1 wherein said container portion and said pouring ring are so adapted to each other whereby the entire cross-section of said at least one pouring opening of said pouring ring is above the upper edge of the mouth opening of said container portion.

6. The crucible assembly as set forth in claim 1 which is substantially of a rotationally symmetrical configuration and which comprises at least four of said pouring openings arranged around the periphery of said pouring ring.

7. The crucible assembly as set forth in claim 1 wherein said pouring openings of said pouring ring are disposed at substantially equal angular spacings from each other.

8. The crucible assembly as set forth in claim 1 wherein all of said pouring openings of said pouring ring are of the same configuration.

9. The crucible assembly as set forth in claim 1 wherein said pouring openings are formed by a spout-like extension portion.

10. A crucible assembly for use in melting small amounts of material particularly for dental, analytical and metallurgical purposes, which comprises:
    a container member for receiving the material and comprised of a peripheral wall portion and a bottom wall portion and having a mouth opening provided at an end of said container member remote from said bottom wall portion, said container member further including an engagement means at an edge about said mouth opening thereof; and a ring member defining an aperture and having an edge portion providing means engageable with said engagement means on said container member thereby to connect said container member to said ring member, the ring member further having at least one pouring opening for a flow of said material from said container portion when said crucible member is rotatable about a middle axis.

11. The crucible assembly as set forth in claim 10 wherein said engagement means on said ring member and on said container member are adapted to permit relative rotary movement between said ring member and said container member, thereby to adjust the relative position of said at least one opening relative to the periphery of said container member.

12. A melting crucible for small amounts of material to be processed therein, comprising a container member for contacting said material formed with an upper portion member having a plurality of selectively usable pouring means for discharge flow of said material from said container member at a plurality of selectible positions therearound, said selectively usable pouring means comprised of a ring operatively connected to said upper portion of said container member and provided with at least two pouring openings, said ring and said container member being rotatable relative to each other thereby to adjust the position of said at least two pouring openings relative to the periphery of said container member thereby to select the position of discharge flow of said material from said container member.

* * * * *